(12) United States Patent
Ford et al.

(10) Patent No.: US 8,299,227 B2
(45) Date of Patent: Oct. 30, 2012

(54) METHOD OF IMMOBILIZING AND STRETCHING A NUCLEIC ACID ON A SUBSTRATE

(75) Inventors: William E. Ford, Stuttgart (DE); Jurina Wessels, Stuttgart (DE); Akio Yasuda, Esslingen (DE)

(73) Assignee: Sony Deutschland GmbH, Köln (DE)

( * ) Notice: Subject to any disclaimer, the term of this patent is extended or adjusted under 35 U.S.C. 154(b) by 0 days.

(21) Appl. No.: 13/243,573

(22) Filed: Sep. 23, 2011

(65) Prior Publication Data

US 2012/0016110 A1 Jan. 19, 2012

Related U.S. Application Data

(62) Division of application No. 10/942,713, filed on Sep. 15, 2004, now Pat. No. 8,058,002.

(30) Foreign Application Priority Data

Sep. 18, 2003 (EP) .................................... 03021204

(51) Int. Cl.
C07H 21/02 (2006.01)
C07H 21/04 (2006.01)
C12M 1/00 (2006.01)

(52) U.S. Cl. ................. 536/23.1; 536/23.33; 536/23.34; 435/283.1

(58) Field of Classification Search ........................ None
See application file for complete search history.

(56) References Cited

U.S. PATENT DOCUMENTS

| | | | | | |
|---|---|---|---|---|---|
| 5,661,028 | A | * | 8/1997 | Foote | 435/287.2 |
| 5,840,862 | A | * | 11/1998 | Bensimon et al. | 536/22.1 |
| 6,060,327 | A | * | 5/2000 | Keen | 506/9 |
| 6,248,539 | B1 | | 6/2001 | Ghadiri et al. | |
| 6,576,478 | B1 | | 6/2003 | Wagner et al. | |
| 6,677,163 | B1 | * | 1/2004 | Boukherroub et al. | 506/17 |
| 6,683,056 | B2 | | 1/2004 | Washburn et al. | |
| 2004/0156108 | A1 | * | 8/2004 | Chou et al. | 359/566 |

FOREIGN PATENT DOCUMENTS

WO  WO 97 06278  2/1997

OTHER PUBLICATIONS

Morita et al. ("Ideal hydrogen termination of Si(001) surface by wet-chemical preparation" Applied Physics Letters. 1995; vol. 67, Issue 18, pp. 2654-2656).*
Kristian M. Roth, et al., "Mesurements of Electron-Transfer Rates of Charge-Storge Molecular Monolayers on Si(100), Toward Hybrid Molecular/Semiconductor Information Storage Devices", J. Am. Chem. Soc., 2003, 125, 505-517.
Carl J. Barrelet, et al., "Surface Characterization and Electrochemical Properties of Alkyl, Fluorinated Alkyl, and Alkoxy Monolayers on Silicon", Langmuir, 2001, 17, 3460-3465.
J.E. Bateman, et al., "A Deuterium Labeling, FTIR, and Ab Initio Investigation of the Solution-Phase Thermal Reactions of Alcohols and Alkenes with Hydrogen-Terminated Silicon Surfaces", J. Phys. Chem. B 2000, 104, 5557-5565.
Dongsheng Xu, et al., "Hydrolysis and silanization of the hydrosilicon surface of freshly perpared porous silicon by an amine catalytic reation", New J. Chem., 2003, 27, 300-306.
Gu-Bo, Li, et al., "Stable and intense blue-green emission in porous silicon achieved by amine immersion and rapid oxidation", Appl. Phys. Lett., 70(10), Mar. 10, 1997.
Namyong Y. Kim, et al., "Thermal Derivatization of Porous Silicon with Alcohols", J. Am. Chem. Soc., 1997, 119, 2297-2298.
Morita, et al., "Ideal hydrogen termination of Si (001) surface by wet-chemical preparation", Applied Physics Letters. 1995. vol. 67, Issue 18, pp. 2654-2656.
Gueroui, et al., "Observation by fluorescene microscopy of transcription on single combed DNA" Proc Natl Acad Sci U S A, Apr. 30, 2002; 99(9):6005-10).
Lin R et al: "Selective extraction of size-fractioned DNA samples in microfabricated electrophoresis devices" Journal of Chromatography A, Elsevier Science, NL, vol. 1010, No. 2, Aug. 29, 2003, pp. 255-268, XP004447879.
Lagally E T et al: "Monolithic integrated microfluidic DNA amplification and capillary electrophoresis analysis system" Sensors and Actuators B, Elsevier Sequoia S.A., Lausanne, CH, vol. 63, No. 3, May 2000, pp. 138-146, XP004198332.
Klein D C G et al. "Ordered stretching molecules of deoxyribose nucleic acid between microfabricated polystyrene lines" Applied Physics Letters, American Institute of Physics, New York, US, vol. 78, No. 16, Apr. 16, 2001, pp. 2396-2398, XP002266390.
Foll H et al., "Formation and application of porous silicon" Materials Science and Engineering R: Reports, Elsevier Sequoia S.A., Lausanne, CH, vol. 39, No. 4, Nov. 1, 2002, pp. 93-141, XP004386810.
Takahagi T et al: "Control of the chemical reactivity of a silicon single-crystal surface using the chemical modification technique" Journal of Applied Physics, Sep. 1, 1990, USA, vol. 68, No. 5, pp. 2187-2191. XP002272280.
Sakaue H. et al: "Scanning tunneling microscopy observation on the atomic sructures of step edges and etch pits on a NH4F-treated Si(111) surface" JPN J. Appl. Phys., vol. 36, 1997, pp. 1420-1423, XP002272281.
Higashi G S et al., "Ideal Hydrogen Termination of the Si(111) Surface" Applied Physics Letters, American Institute of Physics, New York, US, vol. 56, No. 7, Feb. 12, 2990, pp. 656-658, XP000126693.

* cited by examiner

*Primary Examiner* — Christopher M. Babic (74) *Attorney, Agent, or Firm* — Oblon, Spivak, McClelland, Maier & Neustadt, L.L.P.

(57) ABSTRACT

The present invention relates to a method of immobilizing and stretching a nucleic acid on a silicon substrate, to nucleic acids and substrates prepared according to this method, to uses of the method and to uses of the nucleic acid and the substrate.

19 Claims, 6 Drawing Sheets

Heights:
0.79 nm
0.57 nm

Heights:
3.31 nm
1.55 nm

METHOD OF IMMOBILIZING AND STRETCHING A NUCLEIC ACID ON A SUBSTRATE

The present invention relates to a method of immobilizing and stretching a nucleic acid on a silicon substrate, to nucleic acids and substrates prepared according to this method, to uses of the method and to uses of the nucleic acid and the substrate.

A. Stretching and Immobilizing DNA on Hydrophobic Substrates.

Bensimon et al. (1994, 1995) originally developed a process called "molecular combing" for high-resolution genomic studies. The process is strongly dependent on the substrate hydrophobicity and the pH of the solution. Various types of hydrophobic substrates are suitable for molecular combing, including polymers such as polystyrene (PS), polymethylmethacrylate (PMMA), and polycarbonate as well as glass treated with hydrophobic silanes. More recent developments include the use of hydrophobic polymers with substituents that may intercalate DNA (Nakao et al. (2002), Nano Lett. 2, 475). In addition it has been demonstrated that patterning of, e.g., PS provides control over positioning of DNA on the substrate (Klein et al. (2001), Appl. Phys. Lett. 78, 2396).

The stretching of DNA during molecular combing occurs by a "moving meniscus" mechanism. The mechanism by which DNA binds to the hydrophobic surface is uncertain, but it is believed to involve the denaturation of the DNA ends, which exposes the hydrophobic bases and allows them to interact with the surface. This interaction is strong enough to prevent the DNA from being removed during stretching as well as subsequent treatments such as exposure to solutions of DNA-binding molecules.

Molecular combing usually causes double-stranded DNA molecules to elongate approximately 50% beyond their B-form contour lengths. This overstretching may result in a transition of the secondary structure from 13-form to S-form, or it may result in strand dissociation. In either case, overstretching can affect the ability of combed DNA to interact with DNA-binding proteins. Gueroui et al. (2002) recently developed a simple way to avoid DNA overstretching during the combing process by using 1-dodecanol to lower the surface tension of the air-water interface. Several other processes besides molecular combing have been developed for stretching single molecules of DNA. These include elongation by spin-coating, fluid flow, electric field, and convective forces in evaporating droplets.

The principal application of molecular combing and related processes is DNA analysis, including genome sequencing and genetic disease screening. Analysis of stretched and immobilized DNA usually relies on fluorescence labeling and detection by optical microscopy (including scanning near-field optical microscopy (SNOM) or use of zero-mode waveguides), but newer methods such as atomic force microscopy (AFM), scanning tunneling microscopy (STM), and scanning electrochemical microscopy (SECM) have also been used. Other applications of molecular combing and related processes include DNA archiving and metallization.

B. Hydrogen-Terminated Silicon.

Etching with aqueous HF is a key step in producing Si surfaces that are free of contaminants and chemically stable for subsequent processing in the semiconductor industry. Treatment with HF removes the native or thermally grown oxide layer and leaves the surface terminated by silicon hydride (Si—H) groups. The exact nature of the surface generated on single crystal Si wafers depends on the crystal orientation as well as the etching conditions. Dilute (1-2%) aqueous HF treatment of Si(100) provides a dihydride-terminated ($=SiH_2$) surface, while aqueous $NH_4F$ treatment of Si(111) provides a monohydride-terminated ($=SiH$) surface. The latter is terraced, but the terraces are atomically flat (Higashi et al. (1990)).

Both kinds of surfaces are hydrophobic due to the non-polar nature of the Si—H bond.

The H-terminated Si(100) surface is less stable than the Si(111) because the two H atoms in the $=SiH_2$ group are close enough to cause a strong static repulsion force between them. This makes the dihydride-terminated surface more susceptible towards chemical reaction with $H_2O$ ($OH^-$) and the formation of steps or defects. Furthermore, some F-terminating groups are usually also formed during HF treatment, and these are readily hydrolyzed. Morita and Tokumoto (1995) found that hydrolysis could be suppressed by adding HCl to reduce the pH of the HF solution, however the resulting surface was still terraced. Luo et al. (1997) reported very smooth and featureless surfaces (surface roughness in the range of 0.1 nm) for p-type Si(100) substrates that were treated for 1 minute with $HF:H_2O$ 1:50 solution, while Cerofolini et al. (2003) reported that similar treatment results in surfaces having atomically flat terraces of width around 100 nm separated by double-stepped kinks. Therefore it is unclear from the state of the art knowledge whether flat H-terminated surfaces can be produced on Si(100) and how stable such surfaces are under ambient conditions.

The integration and combination of nucleic acid and silicon technologies has been and continues to be the subject of intense research effort. Although several kinds of silicon-based "DNA chips" already exist, none provides a DNA-binding surface that is both flat and electrically conductive. Such substrates would make it possible to detect and analyze DNA by a combination of single-molecule techniques (e.g., STM, AFM, SNOM, and SECM) as well as by electroanalysis. Furthermore, they would be suitable platforms for DNA-based nano-scale electronic devices.

Accordingly, it has been an object of the present invention to provide a method that allows the fabrication of Si-surfaces for use in nucleic acid analysis which are less rough than other surfaces hitherto known. It has also been an object of the present invention to provide for a method that allows to immobilize and stretch nucleic acids as individual molecules on a surface of a substrate. It has furthermore been an object of the present invention to provide a method that allows the fabrication of flat substrates for subsequent immobilization of nucleic acids, which substrates can also be electrically conducting.

All these objects are solved by a method of immobilizing and stretching a nucleic acid on a substrate comprising the steps:

a) providing a silicon substrate
b) applying a solution of ammonium fluoride or of hydrogen fluoride onto a surface of said silicon substrate
c) allowing said solution of ammonium fluoride or hydrogen fluoride to remain on said surface of said silicon substrate for a defined period of time
d) applying a solution of a nucleic acid onto said surface
e) immobilizing and elongating said nucleic acid by a process selected from the group comprising molecular combing, spin-coating, application of a fluid flow, application of an electric field, application of convective forces in an evaporating droplet of said solution of said nucleic acid, and any combination of the aforementioned processes.

In one embodiment, said silicon substrate is derived from a single crystal of doped or undoped silicon, wherein preferably, said single crystal of silicon has a (100) or (111) surface orientation.

In one embodiment, said silicon substrate has a silicon oxide layer on said surface, wherein preferably, said oxide layer is native or thermally grown.

Preferably, said oxide layer has a thickness between 1 nm and 15 µm.

In another embodiment, said silicon substrate is patterned with metal electrodes, wherein preferably, said metal electrodes are made of a material comprising gold.

In one embodiment, said solution of ammonium fluoride is an aqueous solution of $NH_4F$ (ammonium fluoride), preferably with a concentration of 0.1-11 M, more preferably 0.5-5 M, even more preferably 2 M of ammonium fluoride. In one embodiment, said aqueous solution of $NH_4F$ additionally contains $NH_4OH$ at a concentration sufficient to adjust the pH of said aqueous solution to 9-10.

In one embodiment, said solution of hydrogen fluoride is an aqueous solution of HF (hydrogen fluoride), preferably with a concentration of 0.06-6 M, more preferably 0.2-2 M, even more preferably 0.6 M. In one embodiment said aqueous solution of HF additionally contains HCl, preferably at a concentration of 0.01-10 M, preferably 0.03-3 M, more preferably 0.3 M of HCl (final concentration of HCl).

In one embodiment, said defined period of time for which said solution of ammonium fluoride or hydrogen fluoride is allowed to remain on said surface of said silicon substrate is 0.1-60 min, preferably 0.1-30 min, more preferably 0.1-20 min and most preferably 0.1-10 min. The optimal time depends on the thickness of the oxide layer and can readily be determined by someone skilled in the art.

In one embodiment, said nucleic acid is DNA, preferably double-stranded or single-stranded DNA, RNA or PNA, which nucleic acid is alone or in complex with a protein or several proteins, further characterized in that said solution of said nucleic acid is an aqueous solution of nucleic acid.

In one embodiment, steps d) and e) occur concomitantly.

In another embodiment, step e) occurs after step d).

In one embodiment, step e) is performed in the presence of a surface-active agent.

Preferably, said surface-active agent is selected from the group comprising long-chained alcohols, preferably 1-octanol, 1-decanol, or 1-dodecanol.

Preferably, said solution of ammonium fluoride or said solution of hydrogen fluoride is removed from said surface of said silicon substrate before step d).

The objects of the present invention are solved by a nucleic acid on a silicon substrate, which nucleic acid has been prepared according to the method of the present invention.

The objects of the present invention are also solved by a silicon substrate having a nucleic acid immobilized and stretched on one of its surfaces, which substrate has been prepared according to the method of the present invention.

Furthermore, the objects of the present invention are solved by a combination of nucleic acid according to the present invention and of a substrate according to the present invention.

Moreover, the objects of the present invention are solved by the use of a nucleic acid according to the present invention, a silicon substrate according to the present invention and/or a combination of said nucleic acid and said substrate according to the present invention, for the analysis of nucleic acids, in particular sequencing, transcription studies and screening for genetic polymorphisms and/or genetic aberrations, wherein preferably, said nucleic acid analysis is performed by optical microscopy, including fluorescence microscopy, scanning near-field optical microscopy (SNOM), use of zero-mode waveguides, atomic force microscopy (AFM), scanning tunneling microscopy (STM), and scanning electrochemical microscopy (SECM).

The objects of the present invention are also solved by the use of the inventive method for optical microscopy, including fluorescence microscopy, scanning near-field optical microscopy (SNOM), use of zero-mode waveguides, atomic force microscopy (AFM), scanning tunneling microscopy (STM), and scanning electrochemical microscopy (SECM).

As used herein, the terms "(100) surface orientation" and "(111) surface orientation" are meant to designate specific orientations in a single crystal of silicon, which orientations are well known in the art.

The term "silicon substrate" is meant to designate any substrate, wherein a major component is elemental silicon.

The inventors have devised a method which has the following main advantageous features of this invention compared to the state of the art:

Simplicity. The substrate is easily prepared and requires no chemical reagents to bind nucleic acid except for the treatment with ammonium fluoride or hydrogen fluoride, in particular solutions, preferably aqueous solutions of HF or $NH_4F$. No chemical modification of the nucleic acid is required.

Flatness of the substrate. Most substrates used for nucleic acid immobilization are too rough for high resolution imaging of nucleic acid by scanning probe or scanning near-field optical techniques. The method according to the present invention allows the fabrication of flat substrates. Flat substrates, as used herein, are defined as having a mean surface roughness of typically 0.1 nm or less over an area of (1-5) $\mu m^2$ ((100) surface orientation), or typically 0.1 nm or less on a terrace ((111) surface orientation).

Absence of organic layer. Future applications of nucleic acid are expected to include its serving as a template for nanoparticle catalysts for the directed growth of nanowires. The growth conditions are likely to involve high temperatures, so it will be advantageous to avoid using organic films such as polystyrene, polymethacrylate, and/or polycarbonate.

Electrical conductivity. Doped Si is conductive enough to serve as an electrode for electroanalysis and as a substrate for STM. It also allows for electrical gating of nucleic acid-based nanoelectronic devices. Conductive substrates currently used for nucleic acid immobilization require special surface modification processes.

In a preferred embodiment of the method according to the present invention, the following process parameters are used:

Substrates:
Si(100) or Si(111), doped (n- or p-type) or undoped, with native or thermally-grown oxide layer on surface.

HF or $NH_4F$ Treatment:
Si(100): Aqueous HF (0.6 M [0.06-6 M]) that may contain HCl (0.01-10 M) for 0.1-10 min at 0-100° C.
Si(111): Aqueous $NH_4F$ (2 M [0.1-11 M]) that may contain $NH_4OH$ (0.01-10 M) for 0.1-10 min at 0-100° C.

Nucleic Acid:
DNA (double- or single-stranded), RNA, PNA, nucleic acid-protein complexes dissolved in aqueous solution (pH 4-10) with concentration of 1 ng/L to 1 g/L.

Method of Application of Nucleic Acid to Substrate:
For 1 sec to 1 hour at 4-80° C., preferably with elongation of the nucleic acid molecules (via spin coating, molecular combing, fluid flow, electric field, convective forces, etc.), in the presence of a surface-active agent such as long-chained alcohols, preferably 1-octanol, 1-decanol, or 1-dodecanol, if overstretching is to be prevented.

Reference is now made to the figures wherein.

The invention will now be further illustrated by the following example which is given for illustrative, not for limiting purposes.

EXAMPLE

Figure 1:
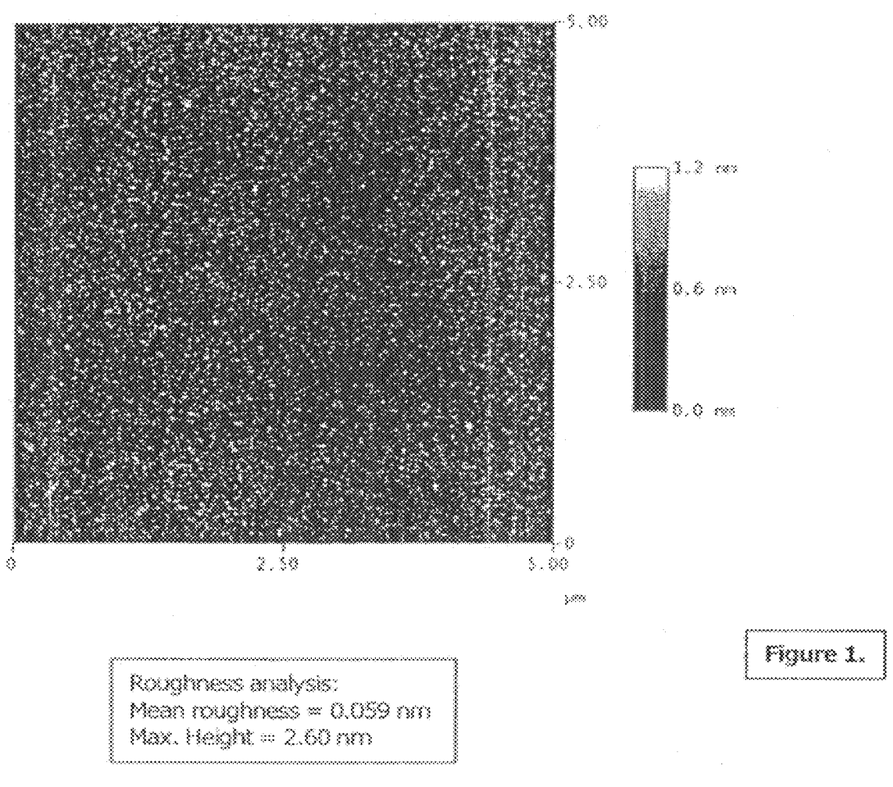
FIG. 1 shows an AFM image of H-terminated Si(100) as prepared according to the method of the present invention. The surface is flat with a roughness similar to the original Si substrate terminated with native oxide.
Figure 2:
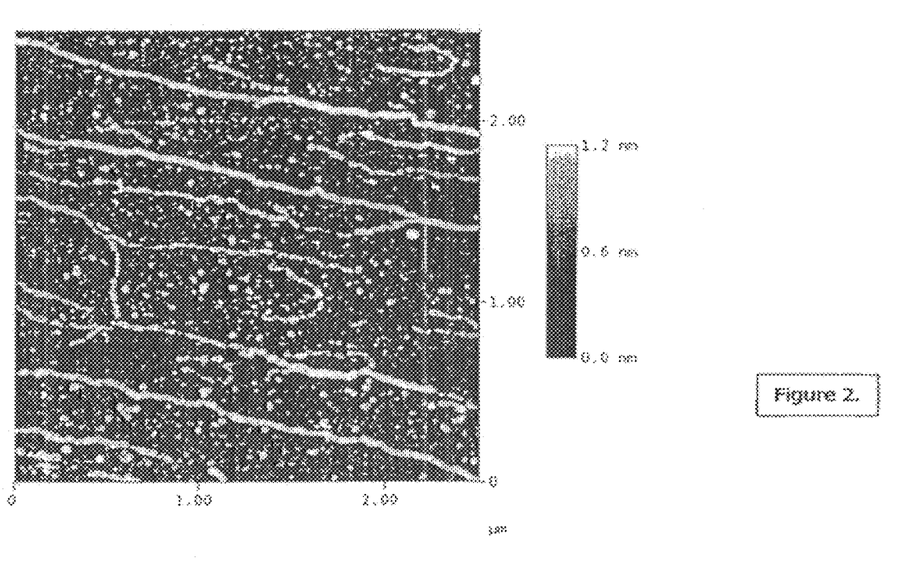
FIG. 2 shows an AFM image of calf thymus DNA immobilized on H-terminated Si(100) according to the Example given below, showing numerous stretched DNA molecules on the surface.
Figure 3:
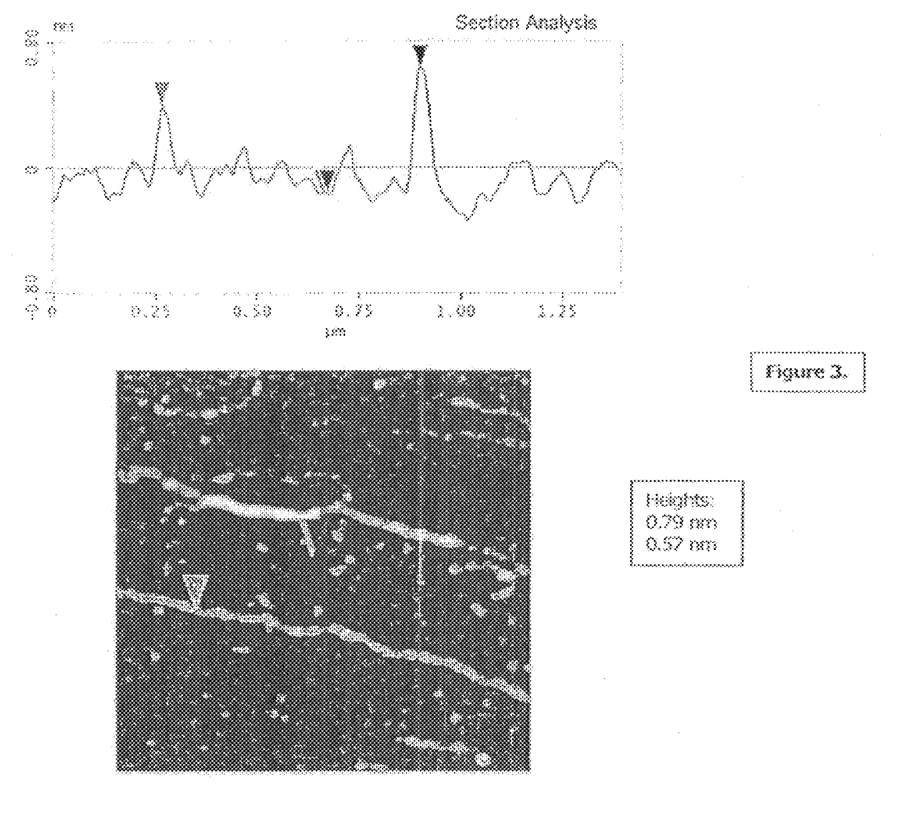
FIG. 3 shows a height profile of the image in FIG. 2. The heights indicate that the DNA molecules occur predominantly as individual and pairs of molecules.
Figure 4:
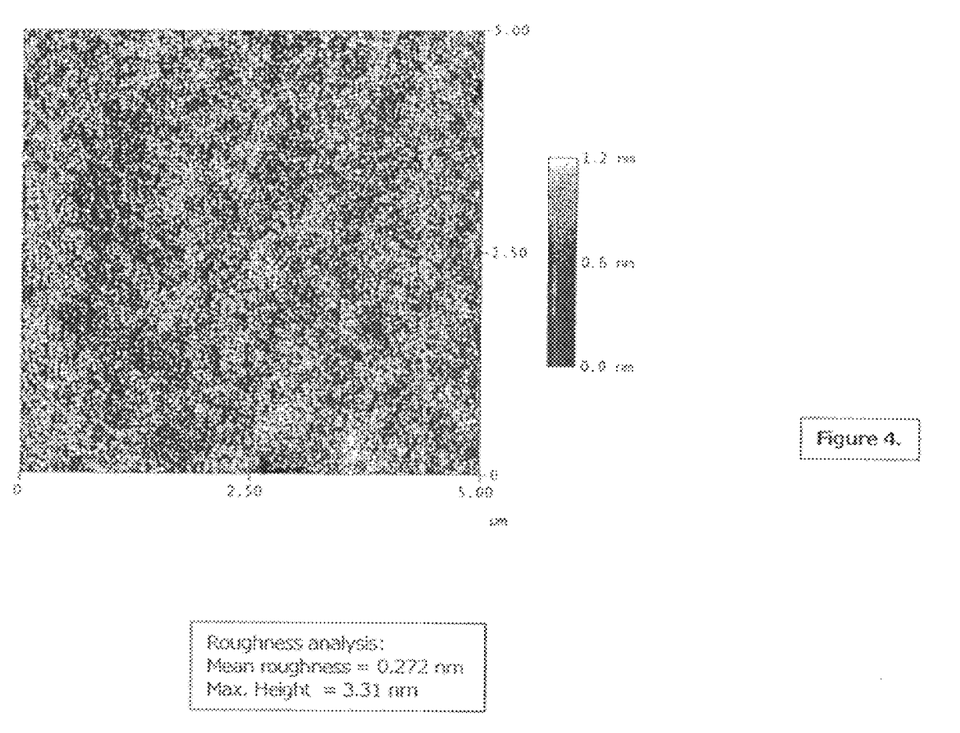
FIG. 4 shows an AFM image of a ca 30-nm thick polystyrene film on mica. The surface roughness is 4-5 times greater than that of the H-terminated Si(100) substrate in FIG. 1.
Figure 5:
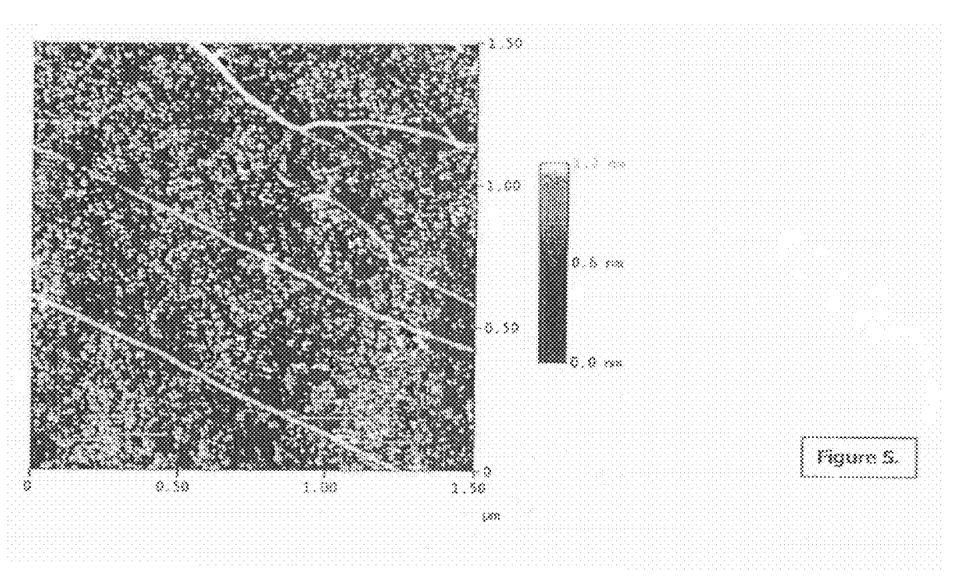
FIG. 5 shows an AFM image of calf thymus DNA immobilized on ca 30-nm thick polystyrene on mica, wherein the nucleic acid has been immobilized by means of molecular combing.
Figure 6:
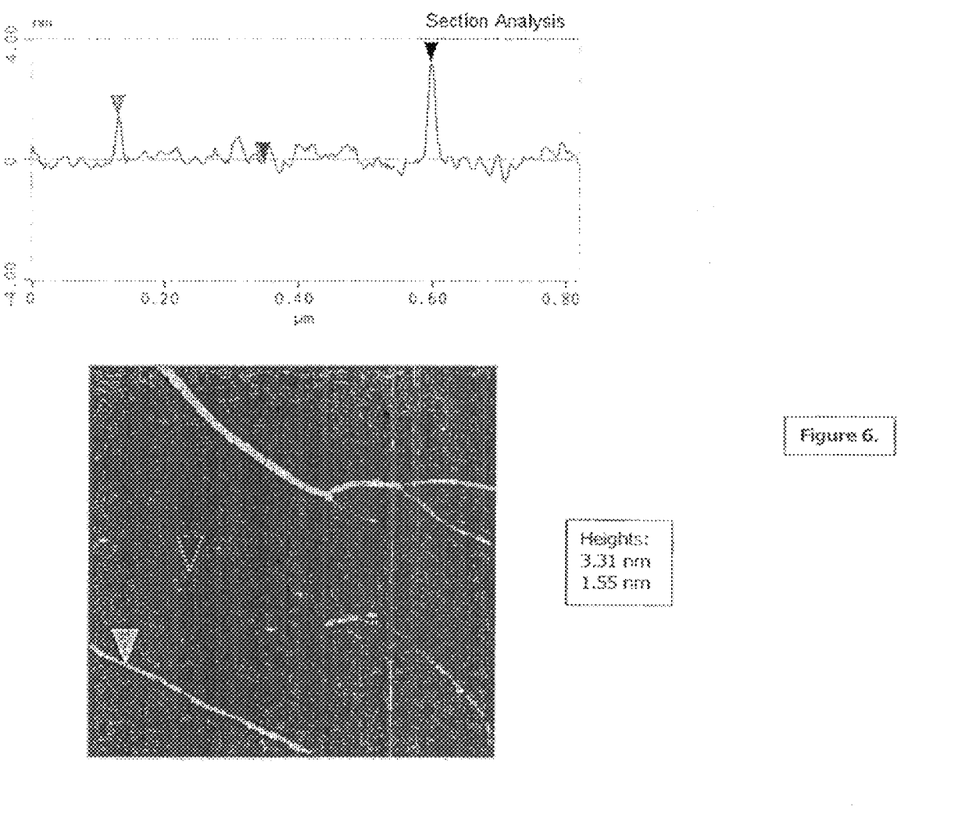
FIG. 6 shows a height profile of the image in FIG. 5. The heights indicate that the DNA molecules occur predominantly as bundles and associations of molecules.

DNA (Type I, sodium salt, "highly polymerized", from calf thymus, Sigma product number D-1501) is dissolved in an aqueous buffer containing 0.010 M sodium phosphate, pH 7.0. The concentration of DNA is 10 mg/L. Concentrated (48 wt-%) aqueous HF is diluted to 1 wt-% with water. The substrate (5 mm×5 mm) is cut from a microelectronic grade n-type Si(100) wafer covered with ~2 nm of native oxide on its polished surface. After cleaning the substrate with an oxygen plasma (3 mbar pressure for 10 minutes), it is immersed into 1 Wt-% HF for 1 minute and then dried with compressed air (see FIG. 1 for an AFM-image of the Si-substrate thus prepared). 50 µL of DNA solution is applied to the resulting H-terminated Si substrate for 1 minute prior to spin coating. The substrate is spun at 4000 rpm for 1 minute, and then rinsed with several drops of water and dried in air while spinning. AFM images (FIGS. 2 & 3) of the sample show individual stretched molecules of DNA (height <1 nm) on a flat surface. In contrast thereto a polystyrene film on mica is 4-5 times rougher, and the nucleic acid immobilized thereon mainly occurs as bundles, judging by the height of the DNA (see FIGS. 4-6).

The features of the present invention disclosed in the specification, the claims and/or in the accompanying drawings, may, both separately, and in any combination thereof, be material for realising the invention in various forms thereof.

What we claim is:

1. A nucleic acid on a silicon substrate, which nucleic acid has been prepared by a method of immobilizing and stretching a nucleic acid on a substrate comprising:
   a) providing a silicon substrate,
   b) applying a solution of ammonium fluoride or of hydrogen fluoride onto a surface of said silicon substrate,
   c) allowing said solution of ammonium fluoride or hydrogen fluoride to remain on said surface of said silicon substrate for a defined period of time,
   d) applying an aqueous solution of a nucleic acid onto said surface of said silicon substrate,
   e) immobilizing said nucleic acid on said substrate and then elongating said nucleic acid by a process selected from the group consisting of molecular combing, spin-coating, application of a fluid flow, application of an electric field, application of convective forces in an evaporating droplet of said solution of said nucleic acid, and any combination of the aforementioned processes,
   wherein said method requires no chemical reagents to immobilize said nucleic acid on said substrate except for the treatment with ammonium fluoride or hydrogen fluoride,
   wherein, if a solution of ammonium fluoride is used, said solution of ammonium fluoride is an aqueous solution of $NH_4F$, and
   wherein, if a solution of hydrogen fluoride is used, said solution of hydrogen fluoride is an aqueous solution of hydrogen fluoride.

2. The nucleic acid on a silicon substrate according to claim 1, wherein step e) occurs after step d).

3. The nucleic acid on a silicon substrate according to claim 1, wherein said silicon substrate is derived from a single crystal of doped or undoped silicon.

4. The nucleic acid on a silicon substrate according to claim 3, wherein said single crystal of silicon has a (100) or (111) surface orientation.

5. The nucleic acid on a silicon substrate according to claim 1, wherein said silicon substrate has a silicon oxide layer on said surface.

6. The nucleic acid on a silicon substrate according to claim 5, wherein said silicon oxide layer is native or thermally grown.

7. The nucleic acid on a silicon substrate according to claim 6, wherein said silicon oxide layer has a thickness between 1 nm and 15 µm.

8. The nucleic acid on a silicon substrate according to claim 1, wherein said silicon substrate is patterned with metal electrodes.

9. The nucleic acid on a silicon substrate according to claim 8, wherein said metal electrodes are made of a material comprising gold.

10. The nucleic acid on a silicon substrate according to claim 1, wherein said defined period of time for which said solution of ammonium fluoride or hydrogen fluoride is allowed to remain on said surface of said silicon substrate is 0.1-60 min.

11. The nucleic acid on a silicon substrate according to claim 1, wherein said nucleic acid is DNA, RNA or PNA, which nucleic acid is alone or in complex with a protein or proteins, wherein said solution of said nucleic acid is an aqueous solution of nucleic acid.

12. The nucleic acid on a silicon substrate according to claim 11, wherein said nucleic acid is DNA and said DNA is double-stranded.

13. The nucleic acid on a silicon substrate according to claim 11, wherein said nucleic acid is DNA and said DNA is single-stranded.

14. The nucleic acid on a silicon substrate according to claim 1, wherein e) is performed in the presence of a surface-active agent.

15. The nucleic acid on a silicon substrate according to claim 12, wherein said surface-active agent is a long-chained alcohol.

16. The nucleic acid on a silicon substrate according to claim 15, wherein said long-chained alcohol is 1-octanol.

17. The nucleic acid on a silicon substrate according to claim 15, wherein said long-chained alcohol is 1-decanol.

18. The nucleic acid on a silicon substrate according to claim 15, wherein said long-chained alcohol is 1-dodecanol.

19. The nucleic acid on a silicon substrate according to claim 1, wherein said solution of ammonium fluoride or said solution of hydrogen fluoride is removed from said surface of said silicon substrate before d).

* * * * *